United States Patent
Monma et al.

(10) Patent No.: US 11,753,751 B2
(45) Date of Patent: Sep. 12, 2023

(54) SURFACE-COLORED GLASS CLOTH AND FIBER-REINFORCED RESIN MOLDED PRODUCT

(71) Applicant: NITTO BOSEKI CO., LTD., Fukushima (JP)

(72) Inventors: Hideaki Monma, Fukushima (JP); Kazunori Sano, Fukushima (JP); Norio Hirayama, Narashino (JP)

(73) Assignee: NITTO BOSEKI CO., LTD., Fukushima (JP)

( * ) Notice: Subject to any disclaimer, the term of this patent is extended or adjusted under 35 U.S.C. 154(b) by 0 days.

(21) Appl. No.: 17/925,290

(22) PCT Filed: Feb. 1, 2021

(86) PCT No.: PCT/JP2021/003528
§ 371 (c)(1),
(2) Date: Nov. 14, 2022

(87) PCT Pub. No.: WO2021/235014
PCT Pub. Date: Nov. 25, 2021

(65) Prior Publication Data
US 2023/0133229 A1    May 4, 2023

(30) Foreign Application Priority Data
May 22, 2020 (JP) .................................. 2020-089536

(51) Int. Cl.
*D03D 15/267* (2021.01)
*B29C 70/22* (2006.01)
*B29K 309/08* (2006.01)

(52) U.S. Cl.
CPC ........... *D03D 15/267* (2021.01); *B29C 70/22* (2013.01); *B29K 2309/08* (2013.01); *B29K 2313/00* (2013.01); *B29K 2995/0026* (2013.01)

(58) Field of Classification Search
CPC .. D03D 15/267; B29C 70/22; B29K 2309/08; B29K 2313/00; B29K 2995/0026
See application file for complete search history.

(56) References Cited

U.S. PATENT DOCUMENTS

2020/0071858 A1    3/2020    Ikejiri et al.

FOREIGN PATENT DOCUMENTS

| | | |
|---|---|---|
| CN | 1332704 A | 1/2002 |
| CN | 104264326 A | 1/2015 |
| JP | H05-269874 A | 10/1993 |
| JP | H06-079722 A | 3/1994 |
| JP | H11-222768 A | 8/1999 |
| JP | 2008-248585 A | 10/2008 |
| JP | 2018-077127 A | 5/2018 |
| JP | 2019-183297 A | 10/2019 |
| JP | 2020-066827 A | 4/2020 |
| WO | 00/021900 A1 | 4/2000 |
| WO | 2016/001986 A1 | 1/2016 |
| WO | 2017/038240 A1 | 3/2017 |
| WO | 2017/168921 A1 | 10/2017 |

OTHER PUBLICATIONS

International Preliminary Report on Patentability and Written Opinion issued in corresponding International Patent Application No. PCT/JP2021/003528 dated Dec. 1, 2022.
Decision to Grant a Patent issued in corresponding Japanese Patent Application No. 2022-524881 dated Jul. 26, 2022.
International Search Report issued in corresponding International Patent Application No. PCT/JP2021/003528 dated Apr. 13, 2021.

*Primary Examiner* — Edward J Cain
(74) *Attorney, Agent, or Firm* — Morgan, Lewis & Bockius LLP

(57) ABSTRACT

A surface-colored glass cloth including a glass cloth which includes a warp and a weft and a plurality of colored portions which are attached to a surface of the glass cloth is disclosed. One colored portion is disposed in each area including one colored point. An average distance D between the adjacent colored points is 0.50 to 10.00 mm. When the number of warp rows is St, a warp widening degree is Et, the number of weft rows is Sy, and a weft widening degree is Ey in the glass cloth, D, St, Et, Sy, and Ey satisfy a formula: $3.3 \leq 100 \times D^{1/2} \times (Et \times Ey)/(St \times Sy) \leq 25.0$.

5 Claims, 6 Drawing Sheets

SURFACE-COLORED GLASS CLOTH AND FIBER-REINFORCED RESIN MOLDED PRODUCT

TECHNICAL FIELD

The present invention relates to a surface-colored glass cloth and a fiber-reinforced resin molded product.

BACKGROUND ART

A strain distribution of a fiber-reinforced resin molded product needs to be measured in order to understand its fatigue state and life. Therefore, for example, a method of testing a fatigue state of a carbon fiber-reinforced resin molded product using a characteristic in which an electric resistance of a carbon fiber increases when the carbon fiber is distorted due to bending or the like has been proposed (Patent Literature 1). A method for measuring a strain distribution by image analysis of a two-dimensional lattice image of a material has also been proposed (Patent Literature 2).

CITATION LIST

Patent Literature

Patent Literature 1: Japanese Unexamined Patent Publication No. H05-269874
Patent Literature 2: International Publication WO 2016/001986

SUMMARY OF INVENTION

Technical Problem

In the fiber-reinforced resin molded product containing a glass cloth as a reinforced fiber, since the glass fiber has an electrical insulation property and a clear two-dimensional lattice image thereof cannot be easily acquired, it has been difficult to measure a strain distribution with high accuracy in a conventional method.

Here, the present invention provides a surface-colored glass cloth capable of measuring a strain distribution of a fiber-reinforced resin molded product with high accuracy by image analysis.

Solution to Problem

An aspect of the present invention is to provide a surface-colored glass cloth including: a glass cloth which includes a warp and a weft and in which the warp and the weft respectively contain a plurality of bundled glass filaments; and a plurality of colored portions which are attached to a surface of the glass cloth.

One colored portion is disposed in each area including one colored point and a plurality of the colored points are arranged on a surface of the glass cloth so that a plurality of rows are formed along a predetermined direction. An average distance D between the adjacent colored points is 0.50 to 10.00 mm. When one colored point is a reference colored point and an area around the reference colored point is equally divided into eight areas by four lines extending in directions of 22.5°, 67.5°, 112.5°, and 157.5° in a clockwise manner with respect to the predetermined direction through the reference colored point, D is an average value of distances between the reference colored point and eight colored points adjacent to the reference colored point in each of the eight areas. The reference colored point is selected from the colored points in which the adjacent colored points exist in each of the eight areas.

When the number of warp rows is St, a warp widening degree is Et, the number of weft rows is Sy, and a weft widening degree is Ey in the glass cloth, D, St, Et, Sy, and Ey satisfy the following formula:

$$3.3 \leq 100 \times D^{1/2} \times (Et \times Ey)/(St \times Sy) \leq 25.0.$$

Each of the number of warp rows and the warp widening degree is calculated by the following formulae:

number of warp rows=(width of glass filament constituting warp)×(number of glass filaments constituting warp)/(width of warp);

and warp widening degree=(width of warp)/{25000 μm/(weaving density of warp)}.

Each of the number of weft rows and the weft widening degree is calculated by the following formulae:

number of weft rows=(width of glass filament constituting weft)×(number of glass filaments constituting weft)/(width of weft); and weft widening degree=(width of weft)/{25000 μm/(weaving density of weft)}.

The weaving density is the number of the warps or wefts per each width of 25 mm of the glass cloth. St and Sy are 0.8 to 8.0 and Et and Ey are 0.30 to 1.20. The width of the glass filament constituting the warp or weft is 3.0 to 11.0 μm. The number of the glass filaments constituting one warp or one weft is 30 to 600. The width of the warp and the weft is 100 to 800 μm. The weaving density of the warp and the weft is 30 to 120/25 mm.

Another aspect of the present invention is to provide a fiber-reinforced resin molded product containing the surface-colored glass cloth and resin impregnated in the surface-colored glass cloth.

A still another aspect of the present invention relates to a fiber-reinforced resin molded product including: a main body which is a fiber-reinforced resin; and an inspection fiber-reinforced resin layer which is provided on a surface of the main body. The inspection fiber-reinforced resin layer contains the surface-colored glass cloth and transparent resin impregnated in the surface-colored glass cloth.

Advantageous Effects of Invention

According to an aspect of the present invention, a surface-colored glass cloth capable of measuring a strain distribution of a fiber-reinforced resin molded product with high accuracy by image analysis is provided. According to another aspect of the present invention, a fiber-reinforced resin molded product capable of measuring a strain distribution by image analysis is provided.

DESCRIPTION OF EMBODIMENTS

Hereinafter, some embodiments of the present invention will be described in detail. However, the present invention is not limited to the following embodiments.

Figure 1:
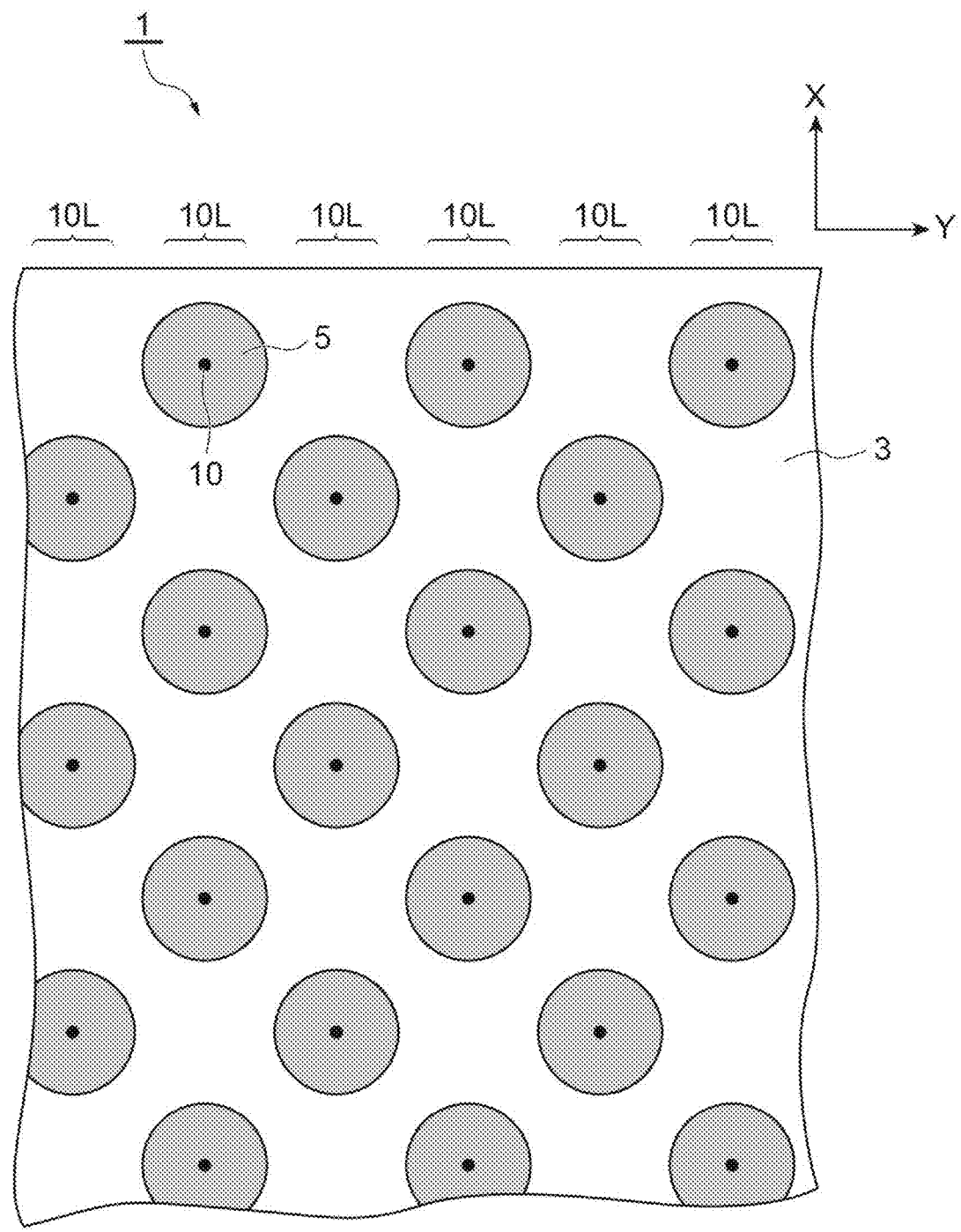
FIG. 1 is a plan view showing an embodiment of a surface-colored glass cloth.

FIG. 1 is a plan view showing an embodiment of a surface-colored glass cloth. A surface-colored glass cloth 1 shown in FIG. 1 includes a glass cloth 3 and a plurality of colored portions 5 attached to the surface of the glass cloth 3. The glass cloth 3 is a woven fabric formed of a plurality of warps aligned in the X direction and a plurality of wefts aligned in the Y direction perpendicular to the X direction and may include a void portion in which the warp and the weft do not exist in the woven fabric although not shown in the drawings. Each of the warp and the weft contains a plurality of bundled glass filaments.

The color of the colored portion 5 is not particularly limited as long as the glass cloth 3 has a color and contrast. Since the uncolored glass cloth 3 is usually white, the colored portion 5 may be black, for example. The colored portion 5 is formed of, for example, resin ink. One colored portion 5 is disposed in each area including one colored point 10. The colored point 10 is usually located at the center of the colored portion 5. The center of the smallest rectangle circumscribing the colored portion 5 may be the colored point 10. The plurality of colored points 10 are arranged on the surface of the glass cloth 3 so that a plurality of rows 10L are formed along a predetermined direction (the X direction). Each row 10L is composed of the plurality of colored points 10 arranged at substantially equal intervals. In the adjacent rows 10L, the colored points 10 are arranged alternately so that the positions in the X direction do not overlap. Examples of the color of the colored portion 5 include red, blue, green, yellow, gray, and white in addition to black.

The glass cloth 3 is typically not colored, but may be colored. For example, the entire glass cloth 3 may be colored black, and the colored portion 5 may be white or the like. The entire glass cloth 3 may be colored white, and the colored portion 5 may be black or the like.

Figure 2:
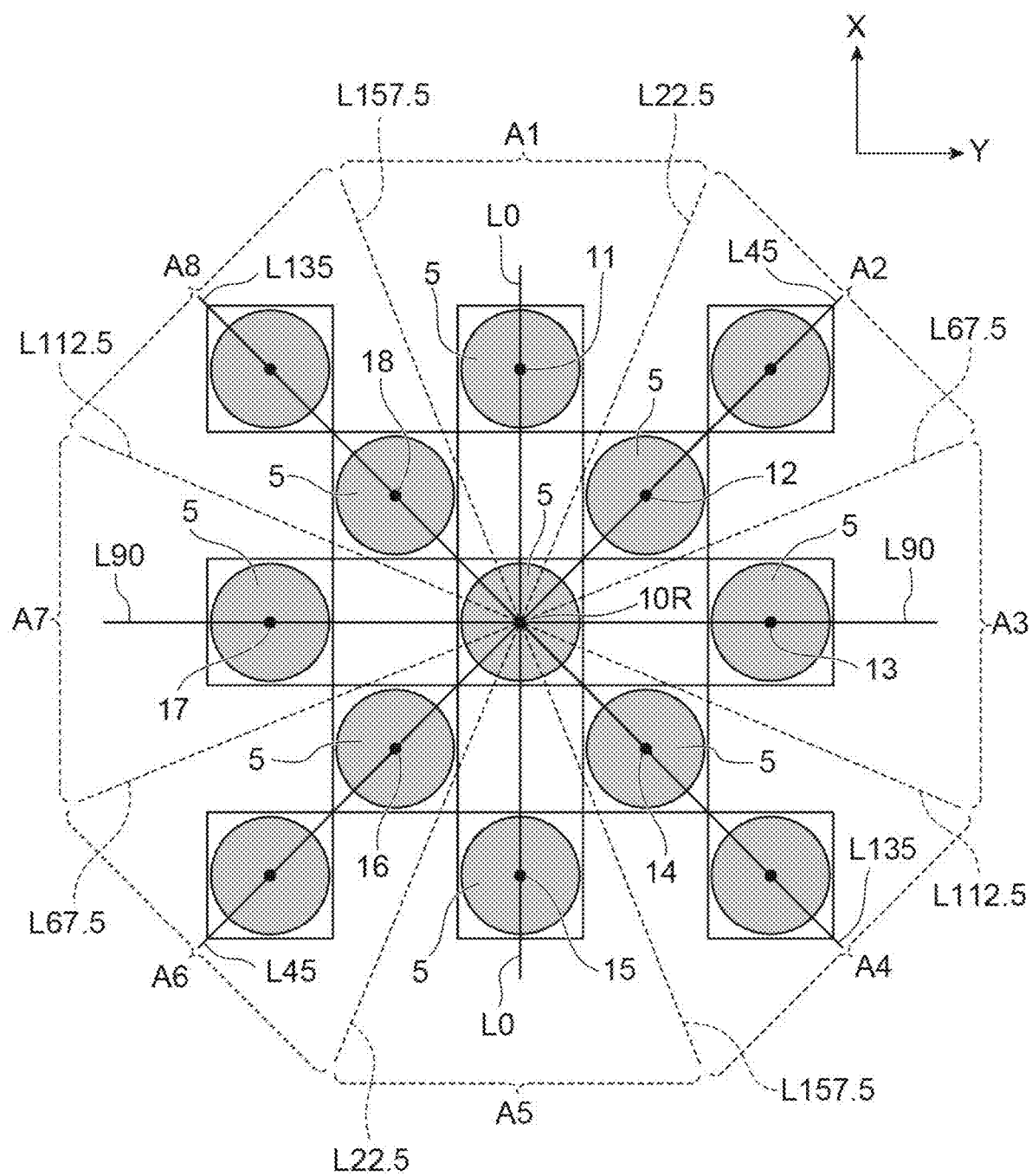
FIG. 2 is a schematic diagram showing an example of an arrangement pattern of a colored portion and a colored point.

An average distance D between the adjacent colored points 10 is 0.50 to 10.00 mm. FIG. 2 is a schematic diagram showing an arrangement pattern of the colored points of the surface-colored glass cloth of FIG. 1. A method of determining the average distance D will be described with reference to FIG. 2. Any one colored point is selected as a reference colored point 10R. An area around the reference colored point 10R is equally divided or divided into eight areas A1, A2, A3, A4, A5, A6, A7, and A8. These eight areas are areas in which an area around the reference colored point 10R is equally divided by four lines L22.5, L67.5, L112.5, and L157.5 passing through the reference colored point 10R. A line L0 is a line extending in the X direction and the lines L22.5, L67.5, L112.5, and L157.5 are respectively lines extending in the directions of 22.5°, 67.5°, 112.5°, and 157.5° in a clockwise manner with respect to the X direction. A colored point 11 and a colored point 15 located on both sides of the reference colored point 10R are respectively arranged in the areas A1 and A5 on the line L0 extending in the X direction through the reference colored point 10R. A colored point 12 and a colored point 16 located on both sides of the reference colored point 10R are respectively arranged in the areas A1 and A6 on a line L45 extending in the direction of 45° with respect to the X direction through the reference colored point 10R. A colored point 13 and a colored point 17 located on both sides of the reference colored point 10R are respectively located in the areas A3 and A7 on a line L90 extending in the direction of 90° with respect to the X direction through the reference colored point 10R. A colored point 14 and a colored point 18 located on both sides of the reference colored point 10R are respectively arranged in the areas A4 and A8 on a line L135 extending in the direction of 135° with respect to the X direction through the reference colored point 10R. An average value of the distances between the reference colored point 10R and eight colored points 11, 12, 13, 14, 15, 16, 17, and 18 adjacent to the reference colored point 10R in each of the eight areas A1 to A8 is an average distance D. Eight colored points 11 to 18 are colored points closest to the reference colored point 10R in each of the eight areas A1 to A8. The reference colored point 10R is selected from the colored points in which adjacent colored points exist in each of the eight areas A1 to A8. The average distance D may be constant or may vary to some extent at the plurality of colored points that can be selected as the reference colored point. The average distance D may vary within ±10% over the entire colored points arranged on the surface of the glass cloth.

The colored portions 5 arranged as shown in FIGS. 1 and 2 can be formed, for example, by printing in which a rectangular (or square) area shown around the colored point is set as a print area.

Figure 3:
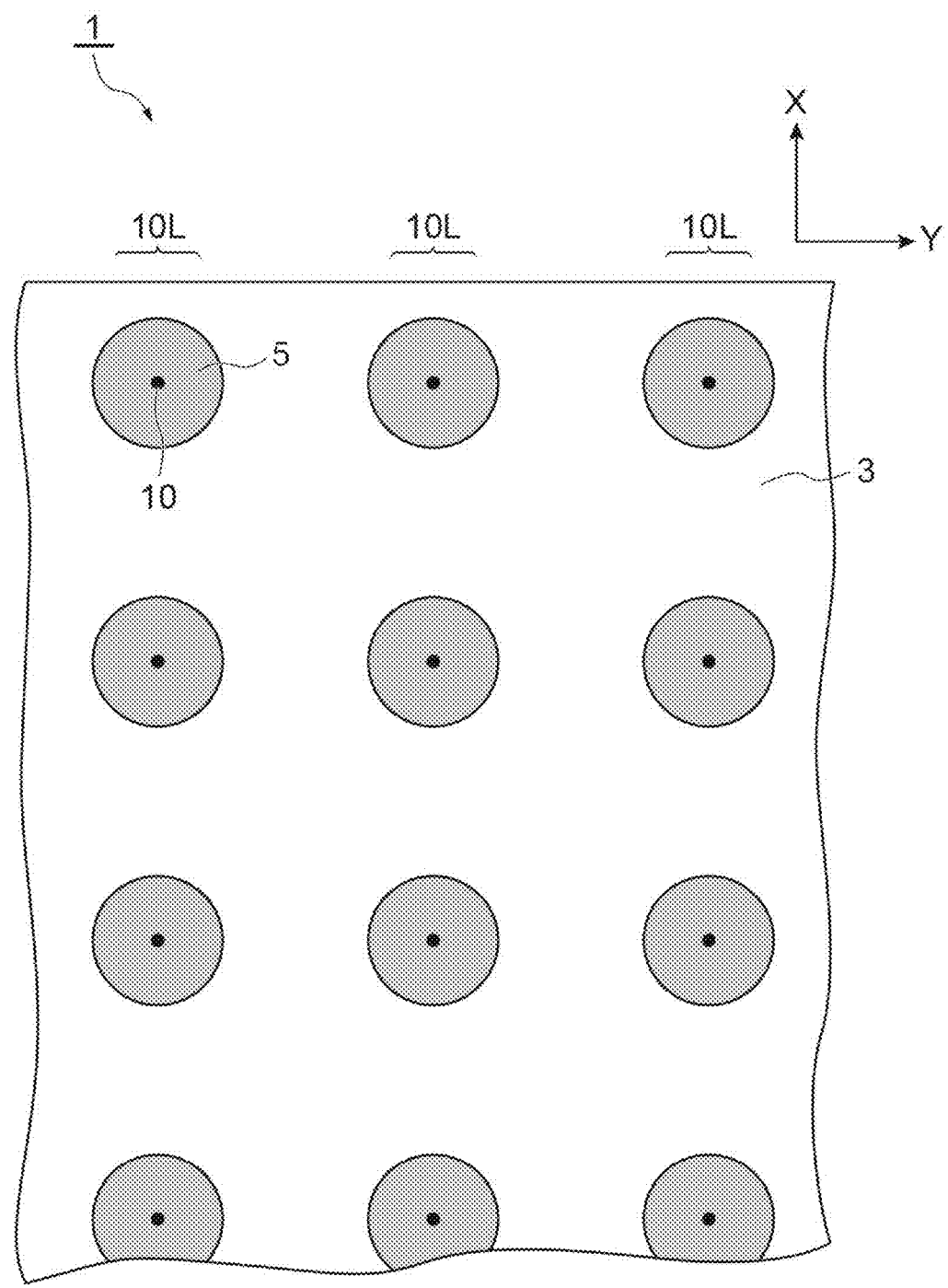
FIG. 3 is a plan view showing an embodiment of a surface-colored glass cloth.
Figure 4:
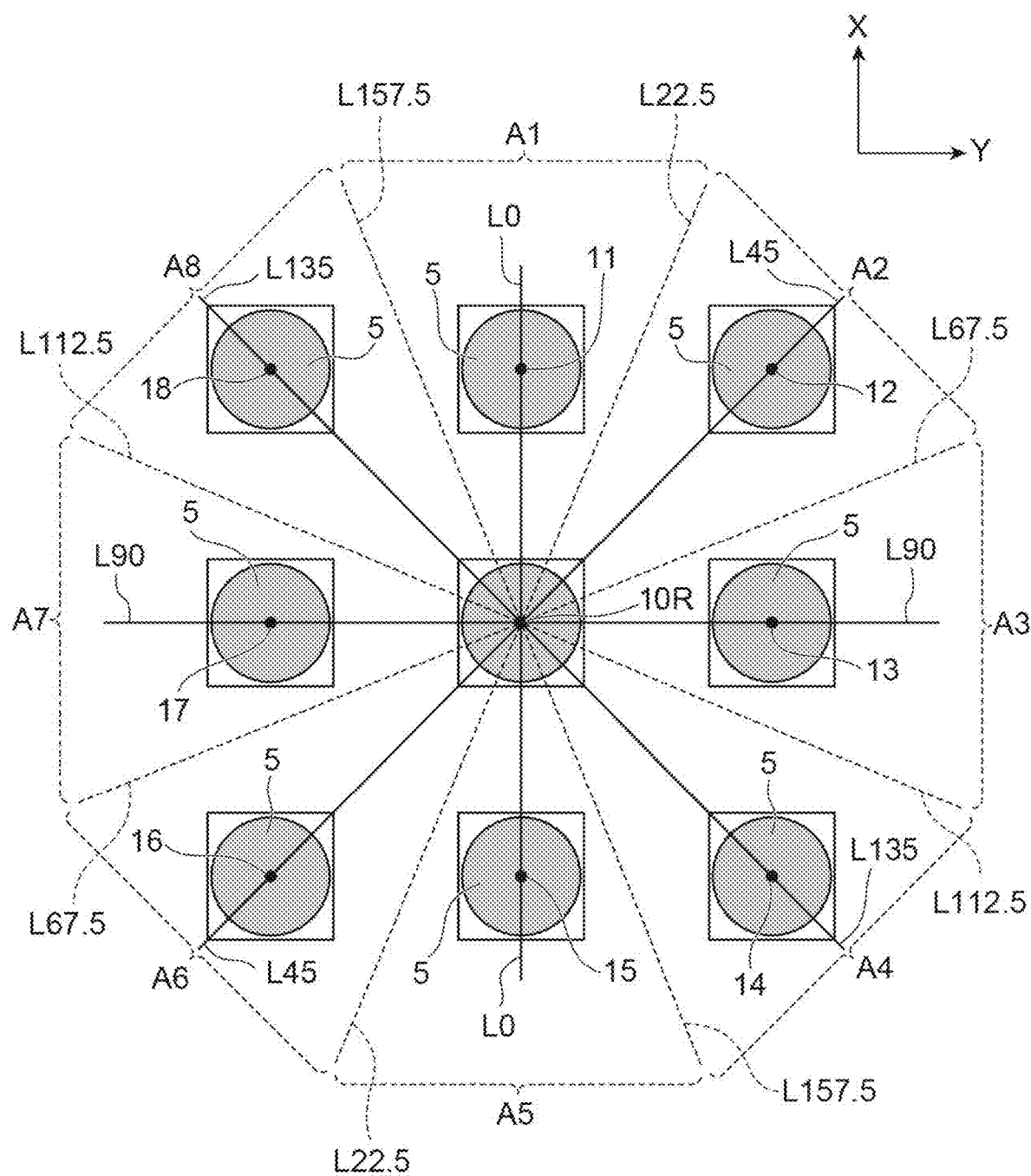
FIG. 4 is a schematic diagram showing an example of an arrangement pattern of a colored portion and a colored point.

FIG. 3 is a plan view showing another embodiment of the surface-colored glass cloth and FIG. 4 is a schematic diagram showing an arrangement pattern of the colored points of the surface-colored glass cloth of FIG. 3. In the case of the embodiments of FIGS. 3 and 4, the plurality of colored points 10 are arranged within the surface of the glass cloth 3 so that the plurality of rows 10L are formed along a predetermined direction (the X direction) and the positions of the colored point 10 in the X direction are the same in the adjacent rows 10L. As shown in FIG. 4, the average distance D between the adjacent colored points 10 is an average value of the distances between the reference colored point 10R and the colored points 11, 12, 13, 14, 15, 16, 17, and 18 adjacent to the reference colored point 10R in each of eight areas A1, A2, A3, A4, A5, A6, A7, and A8 around the arbitrarily selected reference colored point 10R.

In the embodiments shown in FIGS. 1 to 4, the average distance D is 0.50 to 10.00 mm. The average distance D may be 1.00 mm, 1.50 mm or more, 3.00 mm or more, 8.00 mm or less, 6.00 mm or less, or 5.00 mm or less. In these embodiments, the direction of each row 10L matches the warp direction. However, the arrangement direction of the row 10L of the colored point may be a direction other than the warp direction.

Figure 5:
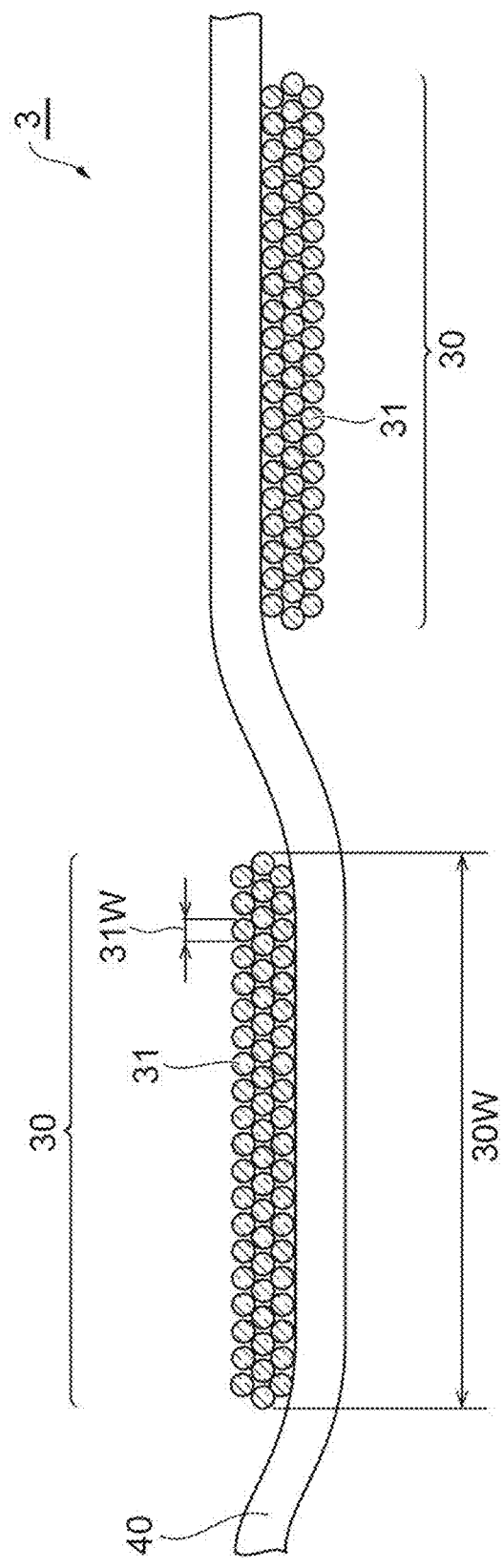
FIG. 5 is a cross-sectional view showing an embodiment of a glass cloth.

FIG. 5 is a cross-sectional view showing an embodiment of the glass cloth constituting the surface-colored glass cloth. FIG. 5 is a cross-sectional view in which the glass cloth 3 is cut in the weft direction. The glass cloth 3 shown in FIG. 5 includes a warp 30 and a weft 40. The warp 30 includes a plurality of glass filaments 31. A width 31W (a maximum width in the cross-section perpendicular to the longitudinal direction) of the glass filament 31 may be 3.0 to 11.0 μm or 3.5 to 9.5 μm. When the glass filament 31 has a circular cross-section, the width 31W is a diameter of the circular cross-section. The number of the glass filaments contained in one warp 30 is 30 to 600 and may be 40 to 450. A width 30W (a maximum width in the cross-section perpendicular to the longitudinal direction) of the warp 30 is 100 to 800 μm and may be 120 to 600 μm. The weaving density of the warp, that is, the number of the warps 30 per each width of 25 mm of the glass cloth in the direction perpendicular to the longitudinal direction of the warp is 30 to 120/25 mm and may be 32 to 100/25 mm. The weft 40 also includes a plurality of glass filaments similarly to the warp 30. The width and number of the glass filaments, the width of the weft, and the weaving density of the weft can be the same as those in the warp. The weaving density of the weft is the number of the wefts 40 per each width of 25 mm of the glass cloth in the direction perpendicular to the longitudinal direction of the weft. The width of the glass filament (the diameter of the glass filament) can be an average value of 50 measured values when the width of the glass filament is measured with a scanning electronic microscope for each of 50 cross-sections of the warp or weft. The number of the glass filaments can be an average value of 50 measured values when the number of the glass filaments constituting the warp or weft is measured with a scanning electronic microscope for each of 50 warps or wefts. The width of the warp and the weft can be an average value of 30 measured values when three samples of 60 mm×100 mm were cut out from the glass cloth and the thread width was measured with a microscope for 30 warp (weft) threads for each sample. The weaving density can be determined by measuring the number of warp rows or wefts per each width of 25 mm of the glass cloth using a textile decomposition mirror in accordance with JIS R 3420: 2013. The glass composition of the glass filament constituting the glass cloth 3 is not particularly limited, and may be E glass, T glass, S glass, NE glass, or L glass. From the viewpoint of excellent versatility, the glass composition of the glass filament constituting the glass cloth 3 may be E glass. The weaving structure of the glass cloth 3 is not particularly limited, and may be a plain weave, a twill weave, or a stain weave. The glass cloth 3 may be a plain weave from the viewpoint of reducing the anisotropy of deformation between the warp direction and the weft direction. An organic substance other than the colored portion 5 such as a silane coupling agent and a surfactant may be attached to the surface of the glass cloth 3.

In the glass cloth 3, the number of warp rows is St, the warp widening degree is Et, the number of weft rows is Sy, and the weft widening degree is Ey. Each of the number of warp rows and the warp widening degree can be calculated by the following formulae:

Number of warp rows=(width of glass filament constituting warp)×(number of glass filaments constituting warp)/(width of warp);

and

Warp widening degree=(width of warp)/{25000 μm/(weaving density of warp)}

Each of the number of weft rows and the weft widening degree is calculated by the following formulae:

Number of weft rows=(width of glass filament constituting weft)×(number of glass filaments constituting weft)/(width of weft); and Weft widening degree=(width of weft)/{25000 μm/(weaving density of weft)}

St and Sy may be 0.8 to 8.0. St and Sy may be 1.0 or more, 2.0 or more, 3.0 or more, 7.0 or less, or 5.0 or less. Et and Ey may be 0.30 to 1.20. Et and Ey may be 0.60 or more, 0.70 or more, 0.80 or more, 1.10 or less, or 1.00 or less.

D, St, Et, Sy, and Ey satisfy the following formula (1):

$$3.3 \leq 100 \times D^{1/2} \times (Et \times Ey)/(St \times Sy) \leq 25.0 \quad (1)$$

The fiber-reinforced resin molded product capable of measuring the strain distribution with high accuracy by image analysis when the composition of the glass cloth and the average distance D are selected so that D, St, Et, Sy, and Ey satisfy this formula. Et and Ey correlate with the size of the void between the warps or wefts. The large Et and Ey mean that the voids between the warps or wefts are small St and Sy correlate with the size of surface irregularities that may occur on the surface of the warp or weft and the thickness of the warp or weft. The small St and Sy mean that the size of surface irregularities that may occur on the surface of the warp or weft is small and the thickness of the warp or weft is thin Here, the small void between the warps or wefts and the small irregularities that may occur on the surface of the warp or weft contributes to the improvement of the accuracy when the colored portion 5 is provided and further contributes to the improvement of the accuracy of the strain distribution measurement. On the other hand, the thin thickness of the warp or weft affects the work accuracy of the coloring process when the colored portion 5 is provided, which leads to a decrease in the accuracy of the colored portion 5. The average distance D correlates with the work accuracy of the coloring process. The value of $100 \times D^{1/2} \times (Et \times Ey)/(St \times Sy)$ reflects such various elements and indicates the accuracy when the colored portion 5 is provided.

From the above-described viewpoint, D, St, Et, Sy, and Ey may satisfy the following formula (2) or (3):

$$6.0 \leq 100 \times D^{1/2} \times (Et \times Ey)/(St \times Sy) \leq 17.0 \quad (2)$$

$$9.5 \leq 100 \times D^{1/2} \times (Et \times Ey)/(St \times Sy) \leq 16.0 \quad (3)$$

The fiber-reinforced resin molded product can be obtained from the surface-colored glass cloth and the resin according to the above-described embodiment. Here, the resin may be a curable resin or a thermoplastic resin. When the resin is the curable resin, the fiber-reinforced resin molded product can be obtained in such a manner that the surface-colored glass cloth according to the above-described embodiment is impregnated with the curable resin by using a press molding method, a hand lay-up molding method, an infusion molding method, an RTM molding method, or the like and the curable resin is cured or semi-cured by heat or light. The fiber-reinforced resin molded product can be also obtained by using a press molding method for a fiber-reinforced resin molded product (prepreg) in which a curable resin is semi-cured. Further, when the resin is the thermoplastic resin, the fiber-reinforced resin molded product can be obtained by using a press molding method, a double belt type continuous press molding method, or the like for one in which a thermoplastic resin film and the surface-colored glass cloth according to the above-described embodiment are alternately laminated.

Examples of the curable resin used as the resin include epoxy resin, unsaturated polyester resin, vinyl ester resin, polyisocyanate resin, polyimide resin, melamine resin, phenol resin, urethane resin, and polyisocyanurate resin. Examples of the thermoplastic resin used as the resin include polystyrene resin, acrylonitrile/butadiene/styrene (ABS) resin, methacrylic resin, polyacetal resin, polyethylene terephthalate (PET) resin, polycarbonate resin, polyallylate (PAR) resin, polyethylene resin, polypropylene resin, vinyl chloride resin, polyamide resin, polybutylene terephthalate (PBT) resin, polyphenylene sulfide (PPS) resin, polyether ether ketone (PEEK) resin, liquid crystal polymer (LCP) resin, fluororesin, polyetherimide (PEI) resin, polysulfon (PSF) resin, polyether sulfone (PES) resin, and polyamide-imide (PAI) resin. The resin may be a resin composition containing additives other than the curable resin and the thermoplastic resin, for example, a low shrinkage agent, a flame retardant agent, a defoaming agent, and the like.

The resin may be transparent resin in order to ensure the visibility of the colored portion 5. The transparent resin means resin having a total light transmittance of 90% or more measured in accordance with JIS-K7375. The transparent resin may be, for example, a curable resin such as an epoxy resin, an unsaturated polyester resin, a vinyl ester resin, a polyisocyanate resin, and a polyimide resin or a thermoplastic resin such as a polystyrene resin, an acrylonitrile/butadiene/styrene (ABS) resin, a methacrylic resin, a polyacetal resin, a polyethylene terephthalate (PET) resin, a polycarbonate resin, and a polyallylate (PAR) resin.

In the above-described fiber-reinforced resin molded product, the ratio of the surface-colored glass cloth to the total amount thereof may be 5 to 70% by mass or 10 to 50% by mass.

Figure 6:
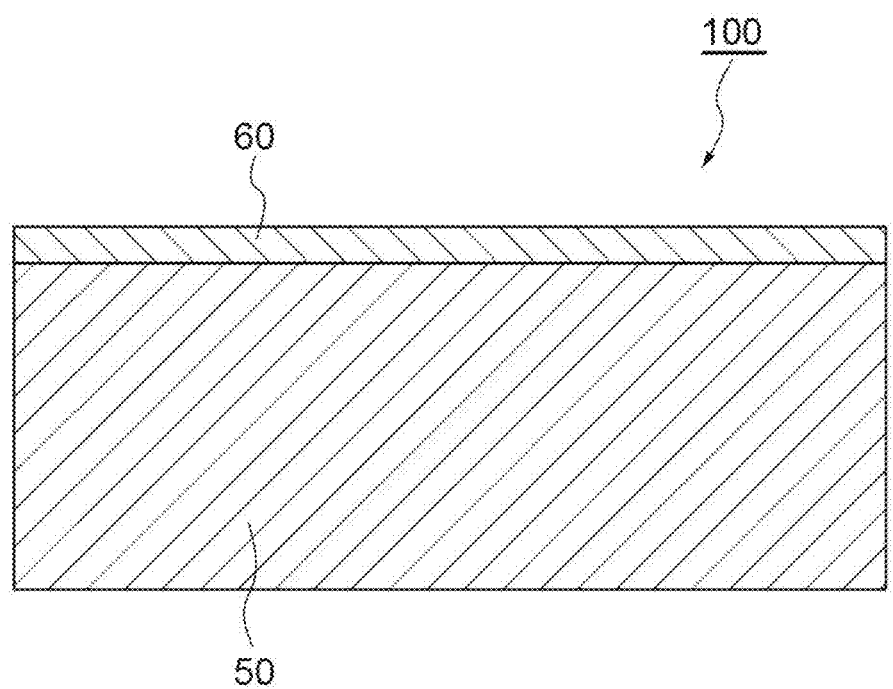
FIG. 6 is a cross-sectional view showing an embodiment of a fiber-reinforced resin molded product.

The fiber-reinforced resin molded product including the inspection fiber-reinforced resin layer for inspecting strain distribution can be obtained by using the surface-colored glass cloth according to the above-described embodiment. FIG. 6 is a cross-sectional view showing an embodiment of the fiber-reinforced resin molded product. A fiber-reinforced resin molded product 100 shown in FIG. 6 includes a main body 50 and an inspection fiber-reinforced resin layer 60 provided on the surface of the main body 50.

The main body 50 is a fiber-reinforced resin containing a reinforced fiber and a resin layer impregnated in the reinforced fiber. The main body 50 may be a product which includes a plurality of fiber-reinforced resin layers including a sheet-shaped reinforced fiber and a resin layer and in which these are laminated. The reinforced fiber constituting the main body 50 is not particularly limited, but may be, for example, a glass fiber, a carbon fiber, an aramid fiber, or a combination thereof. The reinforced fiber may be a non-woven fabric or a woven fabric.

The inspection fiber-reinforced resin layer 60 may be the above-described fiber-reinforced resin molded product including one or more surface-colored glass cloths according to the above-described embodiment and transparent resin impregnated in the surface-colored glass cloth. The surface-colored glass cloth is disposed in a direction in which the colored portion is located on the outer surface side of the fiber-reinforced resin molded product 100. The inspection fiber-reinforced resin layer 60 can be formed by using, for example, a prepreg including a surface-colored glass cloth and transparent resin which is a curable resin impregnated in the surface-colored glass cloth. The transparent resin constituting the inspection fiber-reinforced resin layer 60 may be the same as or different from the resin layer constituting the main body 50. The thickness of the inspection fiber-reinforced resin layer 60 may be, for example, 0.01 to 1.5 mm or 0.05 to 0.5 mm. In the inspection fiber-reinforced resin layer 60, the ratio of the surface-colored glass cloth may be 25 to 80% by mass or 50 to 70% by mass based on the mass of the inspection fiber-reinforced resin layer 60. The inspection fiber-reinforced resin layer 60 does not need to cover the entire surface of the main body 50, but may be provided to cover a portion of the surface of the main body 50 required for inspection. When the transparent resin constituting the inspection fiber-reinforced resin layer 60 and the main body 50 is the same, the boundary between the inspection fiber-reinforced resin layer 60 and the main body 50, that is, the surface of the main body 50 may not be visually clear. In that case, for example, the surface of the smallest rectangular body containing the entire reinforced fiber constituting the main body 50 can be regarded as the surface of the main body 50.

By detecting a change in the position of the colored portion and the like by image analysis of the surface of the inspection fiber-reinforced resin layer 60, it is possible to measure the strain distribution of the fiber-reinforced resin molded product 100 with high accuracy.

EXAMPLES

Hereinafter, the present invention will be described in more detail with reference to examples. However, the present invention is not limited to these examples.

1. Manufacturing of Surface-Colored Glass Cloth

Three types of glass cloths A, B, and C having the configurations shown in Table 1 were prepared. The glass cloths A, B, and C are all plain weave. The glass composition of the glass filaments constituting the glass cloths A, B, and C is E glass.

TABLE 1

|  |  | Glass cloth A | Glass cloth B | Glass cloth C |
|---|---|---|---|---|
| Warp | Width of glass filament [μm] | 7.0 | 9.0 | 4.0 |
|  | Number of glass filaments | 200 | 400 | 50 |
|  | Weaving density [number/25 mm] | 60 | 44 | 95 |
|  | Width [μm] | 346 | 592 | 132 |
|  | Number of warp rows St | 4.0 | 6.1 | 1.5 |
|  | Warp widening degree Et | 0.83 | 1.04 | 0.50 |
| Weft | Width of glass filament [μm] | 7.0 | 9.0 | 4.0 |
|  | Number of glass filaments | 200 | 400 | 50 |
|  | Weaving density [number/25 mm] | 58 | 32 | 95 |
|  | Width [μm] | 399 | 565 | 200 |
|  | Number of weft rows Sy | 3.5 | 6.4 | 1.0 |
|  | Weft widening degree Ey | 0.93 | 0.72 | 0.76 |

On the surface of each glass cloth, a square print area centered on colored points arranged at regular intervals was set in the same arrangement pattern as in FIG. 1 or 3 in which a plurality of rows were formed along the warp direction. The interval between the adjacent colored points in the warp and weft directions and the area of the print area were set as shown in Table 2. Table 2 also shows the average distance D between adjacent colored points. Each print area on the surface of the glass cloth is printed with black resin ink using a printing station type gravure printing tester (manufactured by Kumagai Riki Kogyo Co., Ltd.) and a surface-colored glass cloth having a plurality of black colored portions arranged at regular intervals in the warp and weft directions was obtained. In the case of Comparative Example 2, when the resin ink was printed, the glass cloth was misaligned and the ink was missing. As a result, it was difficult to perform a normal printing operation.

2. Evaluation of Coloring Accuracy

At least 10 colored portions of the surface-colored glass cloth were photographed while approximating a square using a measurement tool of a digital microscope (KH-8700 manufactured by Hirox Co., Ltd.).

A black portion in the captured image was detected using image processing software, and the area was taken as the area of the colored portion. The black portion is the color portion of Mansell N1 to N5 specified in the 2011 F version paint standard color (pocket version) of the Japan Paint Industry Association. The ratio of the print area in which the average value of the area of each colored portion was set was calculated as the coloring accuracy (%).

3. Manufacturing of Fiber-Reinforced Resin Molded Product

Eight carbon cloths (CO6343 manufactured by Toray) were laminated, and one surface-colored glass cloth was laminated on top of them. A laminate composed of the carbon cloth and the surface-colored glass cloth was impregnated with a transparent epoxy resin using an impregnating roll. This laminate was press-molded at 85° C. for 4 hours to prepare a fiber-reinforced resin molded product with a thickness of 2 mm having a fiber-reinforced resin layer including a surface-colored glass cloth on an outermost layer (corresponding to the inspection fiber-reinforced resin layer 60) and the other layer composed of a fiber-reinforced resin layer (corresponding to the main body 50) including a carbon cloth. The ratio of the fiber reinforced material (the carbon cloth and the surface-colored glass cloth) in the fiber-reinforced resin molded product was 60% by mass with respect to the total mass of the fiber reinforced material and the transparent epoxy resin. Further, the ratio of the surface-colored glass cloth in the fiber-reinforced resin layer (corresponding to the inspection fiber-reinforced resin layer 60) including the surface-colored glass cloth was 70% by mass.

4. Strain Measurement Suitability Evaluation Method

A tensile test was performed in which tensile stress was applied to the fiber-reinforced resin molded product in the biaxial directions of X and Y. An image was taken with 600×600 pixels when the amount of tensile strain was 3% in both the X and Y directions. The dimensions of the printed and non-printed areas in the area of 300×300 pixels in the center of the captured image in the X and Y directions were measured and the fluctuation rate (standard deviation/average×100) was calculated from the average and standard deviation of the measured strain (%; ideally 3%). The strain measurement suitability was "A" when the calculated fluctuation rate was 1.0% or less, the strain measurement suitability was "B" when the calculated fluctuation rate was more than 1.0% and 3.0% or less, and the strain measurement suitability was "C" when the calculated fluctuation rate was more than 3.0%.

TABLE 2

|  |  | Examples | | | | | | Com. Examples | |
|---|---|---|---|---|---|---|---|---|---|
|  |  | 1 | 2 | 3 | 4 | 5 | 6 | 1 | 2 |
| Glass cloth |  | A | A | A | A | B | B | B | C |
| Colored point interval [mm] | Warp direction | 2 | 2 | 1 | 1 | 2 | 2 | 1 | 1 |
|  | Weft direction | 2 | 2 | 1 | 1 | 2 | 2 | 1 | 1 |
| Average distance D between colored points [mm] |  | 4.83 | 3.41 | 2.41 | 1.71 | 4.83 | 3.41 | 2.41 | 2.41 |
| $100 \times D^{1/2} \times (Et \times Ey)/(St \times Sy)$ |  | 12.1 | 10.2 | 8.6 | 7.2 | 4.2 | 3.5 | 3.0 | 39.3 |
| Area of print area [mm$^2$] |  | 4 | 4 | 1 | 1 | 4 | 4 | 1 | Difficult printing |
| Area of colored portion [mm$^2$] |  | 3.02 | 2.86 | 0.67 | 0.63 | 1.75 | 1.92 | 0.39 |  |
| Coloring accuracy [%] |  | 75.5 | 71.5 | 66.9 | 63.3 | 43.7 | 48.0 | 39.2 |  |
| Strain measurement suitability |  | A | A | B | B | B | B | C | — |

REFERENCE SIGNS LIST

1: surface-colored glass cloth, 3: glass cloth, 5: colored portion, 10, 11, 12, 13, 14, 15, 16, 17: colored point, 10L: row of colored points, 10R: reference colored point, 30: warp, 30W: width of warp, 31: glass filament, 31W: width of glass filament, 40: weft, 50: main body, 60: inspection fiber-reinforced resin layer, 100: fiber-reinforced resin molded product, A1, A2, A3, A4, A5, A6, A7, A8: area, L22.5, L67.5, L112.5, L157.5: lines extending in directions of 22.5°, 67.5°, 112.5°, and 157.5° in a clockwise manner with respect to predetermined direction through reference colored point.

The invention claimed is:

1. A surface-colored glass cloth comprising:
a glass cloth comprising a warp and a weft, the warp and the weft respectively contain a plurality of bundled glass filaments; and
a plurality of colored portions attached to a surface of the glass cloth,
wherein one colored portion is disposed in each area including one colored point and a plurality of the colored points are arranged on a surface of the glass cloth so that a plurality of rows are formed along a predetermined direction,
wherein an average distance D between the adjacent colored points is 0.50 to 10.00 mm,
wherein when one colored point is a reference colored point and an area around the reference colored point is equally divided into eight areas by four lines extending in directions of 22.5°, 67.5°, 112.5°, and 157.5° in a clockwise manner with respect to the predetermined direction through the reference colored point, D is an average value of distances between the reference colored point and eight colored points adjacent to the reference colored point in each of the eight areas and the reference colored point is selected from the colored points in which the adjacent colored points exist in each of the eight areas,
wherein when a number of warp rows is St, a warp widening degree is Et, a number of weft rows is Sy, and a weft widening degree is Ey in the glass cloth, D, St, Et, Sy, and Ey satisfy the following formula:

$$3.3 \leq 100 \times D^{1/2} \times (Et \times Ey)/(St \times Sy) \leq 25.0,$$

wherein each of the number of warp rows and the warp widening degree is calculated by the following formulae:

number of warp rows=(width of glass filament constituting warp)×(number of glass filaments constituting warp)/(width of warp); and warp widening degree=(width of warp)/{25000 μm/(weaving density of warp)}, wherein each of the number of weft rows and the weft widening degree is calculated by the following formulae:

number of weft rows=(width of glass filament constituting weft)×(number of glass filaments constituting weft)/(width of weft); and weft widening degree=(width of weft)/{25000 μm/(weaving density of weft)}, wherein the weaving density is a number of the warps or wefts per each width of 25 mm of the glass cloth,
wherein St and Sy are 0.8 to 8.0 and Et and Ey are 0.30 to 1.20, and
wherein a width of the glass filament constituting the warp or weft is 3.0 to 11.0 μm, a number of the glass filaments constituting one warp or one weft is 30 to 600, a width of the warp and the weft is 100 to 800 μm, and the weaving density of the warp and the weft is 30 to 120/25 mm.

2. The surface-colored glass cloth according to claim 1, wherein D, St, Et, Sy, and Ey satisfy the following formula:

$$6.0 \leq 100 \times D^{1/2} \times (Et \times Ey)/(St \times Sy) \leq 17.0.$$

3. The surface-colored glass cloth according to claim 1, wherein D, St, Et, Sy, and Ey satisfy the following formula:

$$9.5 \leq 100 \times D^{1/2} \times (Et \times Ey)/(St \times Sy) \leq 16.0.$$

4. A fiber-reinforced resin molded product comprising:
the surface-colored glass cloth according to claim 1; and
resin impregnated in the surface-colored glass cloth.

5. A fiber-reinforced resin molded product comprising:
a main body that is a fiber-reinforced resin; and
an inspection fiber-reinforced resin layer provided on a surface of the main body,
wherein the inspection fiber-reinforced resin layer contains the surface-colored glass cloth according to claim 1 and transparent resin impregnated in the surface-colored glass cloth.

* * * * *